United States Patent
Sakamoto et al.

[11] Patent Number: 6,004,273
[45] Date of Patent: Dec. 21, 1999

[54] ULTRASOUND TRANSMISSION MEDIUM FEED DEVICE FOR ENDOSCOPICALLY INSERTING ULTRASOUND PROBE

[75] Inventors: Toshio Sakamoto; Toshizumi Tanaka; Hiromu Itoi; Masatoshi Yoshihara, all of Omiya, Japan

[73] Assignee: Fuji Photo Optical Co., Ltd., Omiya, Japan

[21] Appl. No.: 09/152,786

[22] Filed: Sep. 14, 1998

[30] Foreign Application Priority Data

Sep. 22, 1997 [JP] Japan ................................... 9-273290

[51] Int. Cl.⁶ ...................................................... A61B 8/12
[52] U.S. Cl. .......................... 600/459; 600/466; 600/462; 606/46
[58] Field of Search ..................................... 600/123, 146, 600/107, 449, 463, 472, 117, 471; 604/22; 607/99, 101, 122, 116, 119; 606/41, 108, 169; 347/75

[56] References Cited

U.S. PATENT DOCUMENTS

| | | | |
|---|---|---|---|
| 4,034,744 | 7/1977 | Goldberg | 600/445 |
| 4,375,818 | 3/1983 | Suwaki et al. | 600/463 |
| 4,565,724 | 1/1986 | Silwa, Jr. et al. | 600/459 |
| 4,748,985 | 6/1988 | Nagasaki | 600/445 |
| 4,844,080 | 7/1989 | Frass et al. | 600/437 |
| 5,044,788 | 9/1991 | Dias et al. | 600/459 |
| 5,372,138 | 12/1994 | Crowley et al. | 600/463 |
| 5,596,991 | 1/1997 | Tanaka | 600/462 |

*Primary Examiner*—Marvin M. Lateef
*Assistant Examiner*—Ali M. Imam
*Attorney, Agent, or Firm*—Oblon, Spivak, McClelland, Maier & Neustadt, P.C.

[57] ABSTRACT

An ultrasound transmission medium feed device particularly for an endoscopically inserting ultrasound probe adapted to be introduced into a body cavity through and under the guidance of one of biopsy channels provided on an endoscope. The ultrasound transmission medium feed device essentially comprises: a balloon fitted on a base end portion of an ultrasound scanner head fixedly in a hermetically sealed state in such a way as to wrap in an end housing of the scanner head; a fluid inlet-outlet passage provided on the base end portion of the ultrasound scanner head for charging and discharging an ultrasound transmission medium into and out of the balloon through a communicating port; and a pressurizing feed tube adapted to be placed in another biopsy channel of the endoscope and disconnectibly connectible at a fore distal end portion thereof with the fluid inlet-outlet passage on the ultrasound scanner head, the pressurizing feed tube having a pressurizing member in association with a proximal end portion thereof for pressurizing or depressurizing the ultrasound transmission medium to be supplied to the inlet-outlet passage on the ultrasound scanner head of the probe.

7 Claims, 9 Drawing Sheets

ULTRASOUND TRANSMISSION MEDIUM FEED DEVICE FOR ENDOSCOPICALLY INSERTING ULTRASOUND PROBE

FIELD OF THE ART

This invention relates generally to an ultrasound examination system having an endoscopically inserting probe, and more particularly to an ultrasound transmission medium feed device for an endoscopically inserting ultrasound probe, which can promptly and efficiently charge or discharge an ultrasound transmission medium into or out of a balloon which is fitted on an ultrasound scanner head at the distal end of the probe, for inflating the balloon with the ultrasound transmission medium or deflating same into a contracted state.

PRIOR ART

In connection with mechanical scan type ultrasound probes employing an ultrasound transducer element which is scanned mechanically over a certain range at the time of acquisition of information on internal body tissues in a particular region of interest, it has been known in the art to use the so-called endoscopically inserting ultrasound probe which is designed to be introduced into a body cavity through a biopsy or instrument channel of an endoscope, using the endoscope as a guide means. The ultrasound probe of this sort has an ultrasound scanner assembly, including an ultrasound transducer element, attached to a distal end of an elongated flexible cord. The ultrasound probe is connected at its proximal end to an ultrasound image observation terminal, which has a drive circuit for the ultrasound transducer element along with an ultrasound signal processor for processing return echoes of transmitted ultrasound signals into ultrasound images for display on a monitor screen. The ultrasound probe may be integrally connected to the ultrasound image observation terminal but normally it is provided as a separate component and adapted to be disconnectibly connected to the ultrasound image observation terminal either directly or through a probe control unit which is connected between the ultrasound probe and the ultrasound image observation terminal for the purpose of controlling operations of the ultrasound transducer element on the scanner assembly at the distal end of the flexible cord. Accordingly, the flexible cord of the probe is provided with a tail end connector at its proximal end thereby to connect the ultrasound transducer element electrically with the ultrasound image observation terminal.

When introducing an ultrasound probe by using an endoscope as a guide, it is the general practice to use a biopsy channel which is provided on and through an insertion instrument of the endoscope for introduction of a bioptic or surgical instrument, for example, such as forceps. The insertion instrument of the endoscope is usually formed in as small a diameter as possible to ensure smooth insertion into a body cavity and to lessen the pains on the part of the patient. Therefore, normally the above-mentioned biopsy channel is extremely small in diameter and can permit passage of only an ultrasound probe which is likewise extremely small in diameter.

On the other hand, the output power and frequency of the ultrasound probe are greatly influenced by the size of an ultrasound transducer element which is mounted on a scanner assembly at the distal end of the ultrasound probe. In this regard, although an ultrasound transducer element of a large size is not necessarily required in the case of an ultrasound examination of a region immediately beneath the mucous, it is desirable for the ultrasound probe to be equipped with as large an ultrasound transducer element as possible at the time of scanning deeper regions through an intracavitary wall. However, normally the size of the ultrasound transducer element is limited by the inside diameter of the biopsy channel on the endoscope. If the tail end connector and flexible cord of an ultrasound probe are made thinner than the inside diameter of an endoscopic biopsy channel, the ultrasound probe can be placed in the biopsy channel inversely from the tail end connector through an exit opening at the distal or front end of the endoscopic insertion instrument, and the ultrasound probe can employ a bulky scanner assembly with a large ultrasound transducer element as compared with the endoscopic biopsy channel. An ultrasound probe of this type needs to be placed in an endoscopic biopsy channel of an endoscope in a preparatory stage before inserting the endoscope into a body cavity.

For a mechanical scan, an ultrasound transducer element on a scanner assembly at the nose end of the ultrasound probe is mechanically moved in a predetermined direction, for example, linearly in the axial direction of the flexible cord in the case of a linear scan and rotationally in the radial direction in the case of a radial scan. At the time of a linear scan, the ultrasound transducer element is moved in the axial direction by mechanically pushing back and forth a proximal end portion of the flexible cord, which is led out of an endoscopic biopsy channel, more specifically, by pushing back and forth cable means which is fitted in the flexible cord. In contrast, at the time of a radial scan, an ultrasound transducer element needs to be driven into rotation through a rotation transmission means such, for instance, through a flexible coil shaft which is constituted by tightly wound metal wire coils. In order to ensure high transmission efficiency, it is desirable for the flexible transmission shaft to be a double coil shaft which is constituted by inner and outer coils. A flexible transmission shaft of this sort is fitted in a flexible sheathing tube, and internally provides a passage for a signal cable (normally a coaxial cable) to or from the ultrasound transducer element.

When transmitting and receiving ultrasound signals through an intracavitary wall, it is very likely that the path of ultrasound signals be intervened by an air gap unless the ultrasound transducer element is held in intimate contact with the intracavitary wall. As well known in the art, ultrasound signals undergo attenuation to a considerable degree while in transmission in air. Therefore, arrangements should be made to exclude intervention of air between an ultrasound transducer element and an intracavitary wall. Nevertheless, in the case of an ultrasound examination for an internal region immediate beneath the mucous of an intracavitary wall, for example, an ultrasound transducer element is required to be located in the socalled stand-off position, maintaining a predetermined spaced relation with the opposing intracavitary wall. Since the ultrasound transducer element is maintained in a non-contacting position, in this case an air gap inevitably exists at least in part of the path of ultrasound signal transmission. In such a case, it has been the usual practice to supply an ultrasound transmission medium into a balloon which is fitted on the ultrasound scanner assembly at the distal end of the probe, thereby inflating the balloon until it is abutted against the opposing intracavitary wall to stop the air gap.

The ultrasound probe is placed in an endoscopic biopsy channel within an endoscopic insertion instrument in a preparatory stage prior to introduction of the endoscopic insertion instrument into a body cavity, in such a way that the ultrasound scanner is projected forwardly from the distal end of the endoscopic insertion instrument. Accordingly, from the standpoint of easy maneuverability of the endoscopic insertion instrument and lessening pains on the part of the patient, it is desirable to hold the balloon still in a contracted state. For this purpose, it is only after the endoscopic insertion instrument has reached an aimed position within a body cavity that an ultrasound transmission medium is supplied into the balloon on the ultrasound scanner assembly. As a route of supplying an ultrasound transmission medium to the balloon, it is conceivable to use the flexible cord of the ultrasound probe. However, since the flexible cord and its tail end connector are too small in diameter to contain connections for passages which supply and discharge an ultrasound transmission medium to and from the balloon. Further, especially in the case of a radial scan type ultrasound probe, the flexible cord contains within a flexible sheathing tube a flexible transmission shaft, which consists of double layers of tightly wound coils, along with a cable which is passed through an internal space of the flexible transmission shaft, leaving almost no spaces which are sufficient for providing flow passages therein for supplying an ultrasound transmission medium promptly to and from the balloon. Therefore, in inflating the balloon to a predetermined degree, it usually takes a long period of time despite increased pains on the part of the patient.

SUMMARY OF THE INVENTION

With the foregoing situations in view, it is an object of the present invention to provide an ultrasound transmission medium feed device for an endoscopically inserting ultrasound probe, which can charge or discharge an ultrasound transmission medium into and out of a balloon fitted on an ultrasound scanner head of the probe within a body cavity, promptly in a facilitated manner.

It is another object of the present invention to provide an ultrasound transmission medium feed device for an endoscopically inserting ultrasound probe, which allows to secure a broad flow passage for an ultrasound transmission medium to be supplied to and from a balloon fitted on an ultrasound scanner head at the distal end of the probe.

As mentioned above, the present invention concerns an ultrasound transmission medium feed device particularly for use with an ultrasound examination system having an endoscopically inserting ultrasound probe adapted to be introduced into a body cavity through and under the guidance of one of biopsy channels provided on an endoscope. The ultrasound probe has an ultrasound scanner head at the distal end of an elongated flexible cord, which accommodates an ultrasound transducer element within an end housing of such a large size as to necessitate to place the ultrasound probe in one biopsy channel of the endoscope from the opposite proximal end of the flexible cord terminated with a thin and narrow tail end connector capable of passing through the endoscopic biopsy channel. The ultrasound transmission medium feed device essentially comprises: a balloon fitted on a base end portion of an ultrasound scanner head fixedly in a hermetically sealed state in such a way as to wrap in an end housing of the scanner head; an inlet-outlet passage provided on the base end portion of the ultrasound scanner head for charging and discharging an ultrasound transmission medium into and out of the balloon through a communicating port; and a pressurizing feed tube adapted to be placed in another biopsy channel of the endoscope and disconnectibly connectable at a fore distal end portion thereof with the inlet-outlet passage on the ultrasound scanner head, the pressurizing feed tube having a pressurizing member in association with a proximal end portion thereof for pressurizing or depressurizing the ultrasound transmission medium to be supplied to the inlet-outlet passage on the ultrasound scanner head of the probe.

In this instance, since a balloon is fitted on the ultrasound scanner head, it is suitable to use the ultrasound probe for radial scans, rotating the ultrasound transducer element in the radial directions on the head. However, if desired, the probe can be arranged to make linear scans in the axial direction thereof.

In order to make the pressurizing feed tube of the feed device easily disconnectible or separable from the inlet-outlet passage on the scanner head, it is desirable to connect these parts by threaded engagement of screw members or by magnetic attraction. Besides, at least the inlet-outlet passage on the ultrasound scanner head is preferred to have an inwardly converging tapered wall thereby to urge a distal end portion of the pressurizing feed tube into a coaxially aligned position in the passage. The ultrasound transmission medium feed device may further include a check valve in the inlet-outlet passage, which is adapted to reverse the flow direction of the ultrasound transmission medium when a pressure differential higher than a preset value is developed due to a pressure increase or reduction on either side of the valve.

BRIEF DESCRIPTION OF THE DRAWINGS

The above and other objects, features and advantages of the present invention will become apparent from the following particular description of the invention, taken in conjunction with the accompanying drawings which show by way of example some preferred embodiments of the invention and in which.

DESCRIPTION OF PREFERRED EMBODIMENTS

Figure 1:
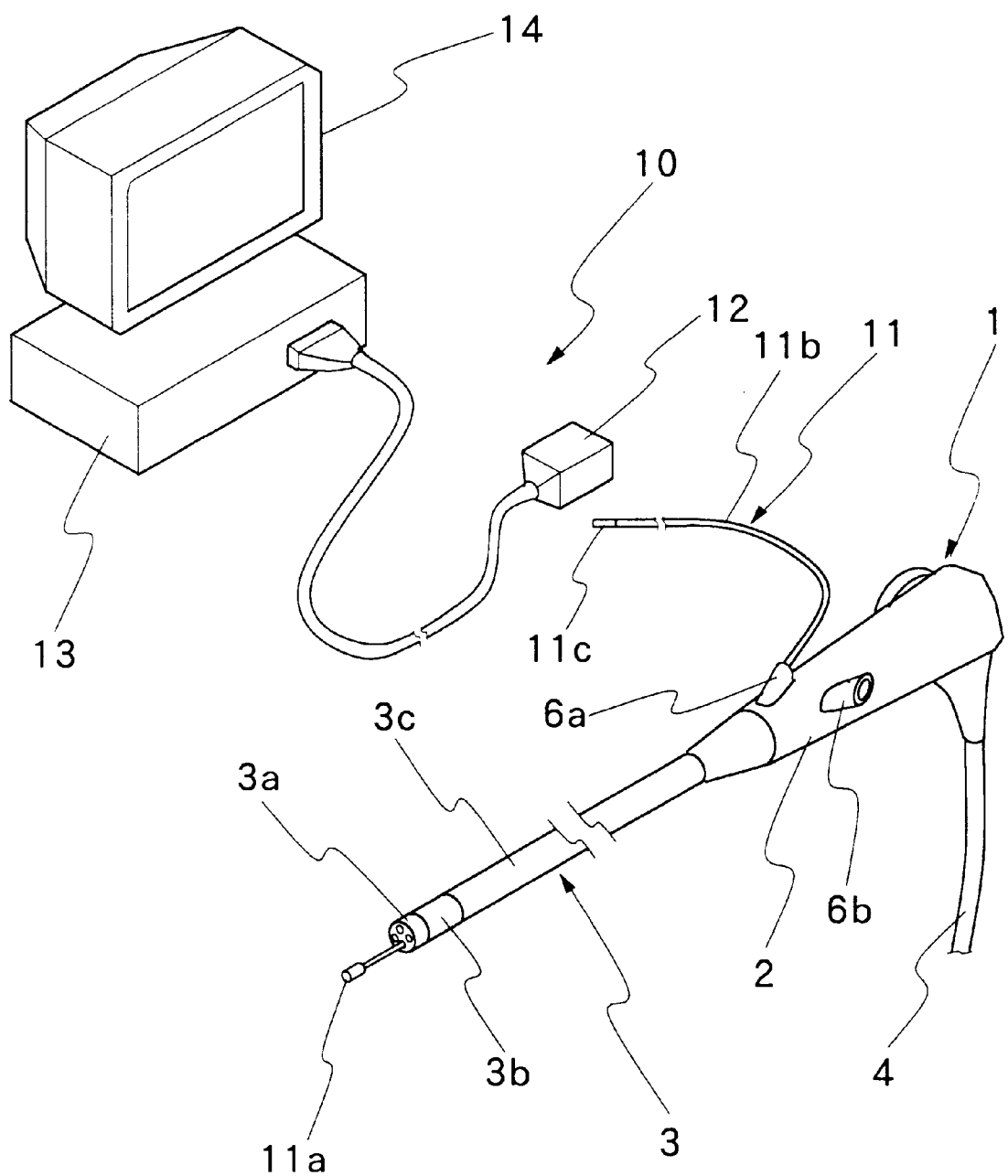
FIG. 1 is a schematic perspective view of an ultrasound examination system employing an endoscopically inserting ultrasound probe, and an endoscope with biopsy channels in its insertion instrument capable of guiding the ultrasound probe into a body cavity.
Figure 2:
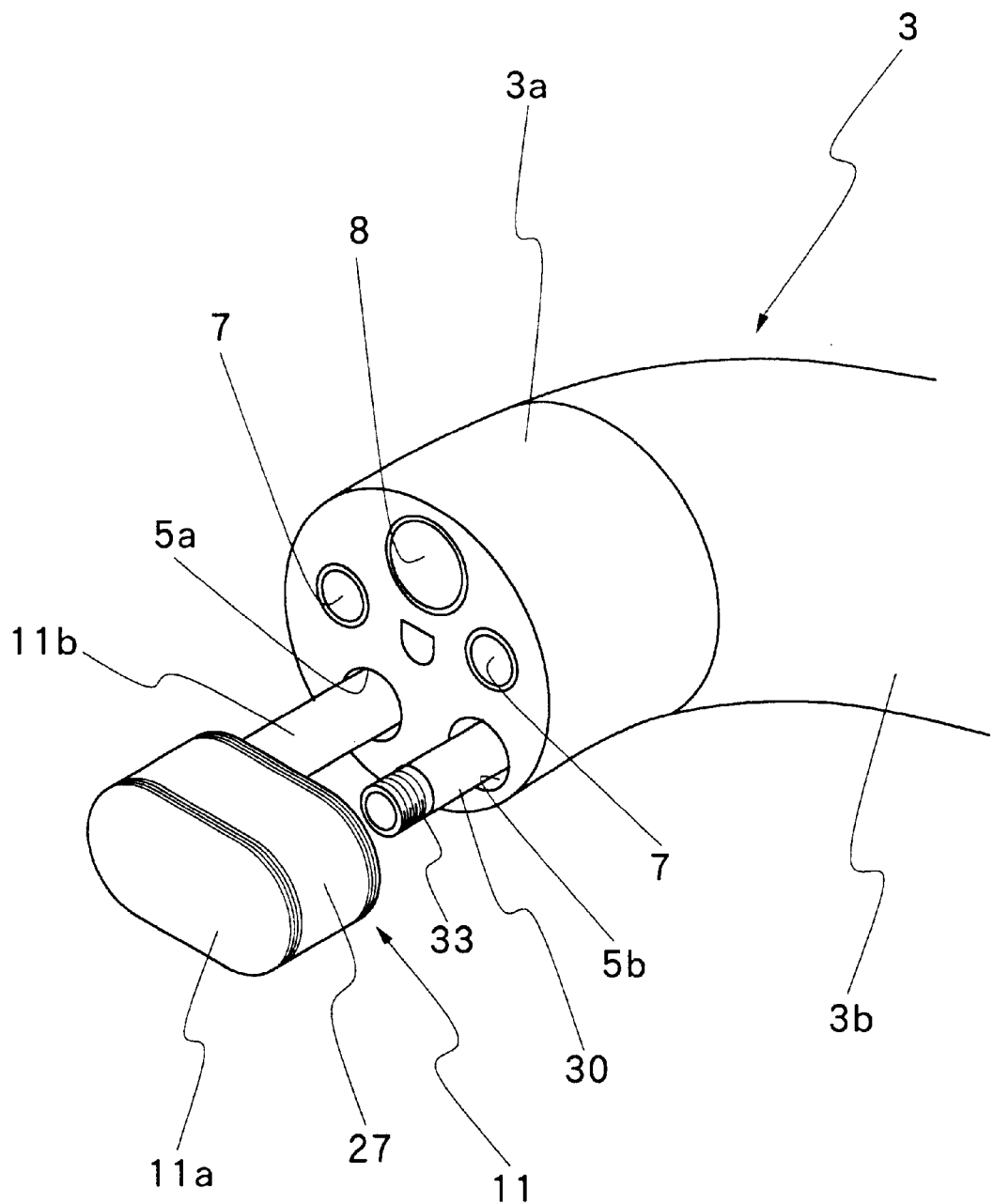
FIG. 2 is a fragmentary perspective view of a fore end portion of an ultrasound probe and an ultrasound transmission medium feed device according to the present invention, which are placed in biopsy channels of an endoscopic insertion instrument.

Hereafter, the present invention is described more particularly by way of its preferred embodiments with reference to the accompanying drawings. Illustrated in FIG. 1 is the general layout of an ultrasound examination system having an endoscopically inserting ultrasound probe placed in a biopsy channel of an endoscope which serves as a guide means for the ultrasound probe, and in FIG. 2 is a fore end portion of the ultrasound probe extended out of an exit opening of the biopsy channel at the distal end insertion instrument.

In these figures, denoted at 1 is an endoscope, and at 10 is an ultrasound examination system. The endoscope 1 has an insertion instrument 3 extended forward from a manipulating grip 2. The endoscopic insertion instrument 3 is largely composed of a distal end section 3a, an angle section 3b and a flexible section 3c successively from its fore end. Led out from the manipulating grip 2 of the endoscope 1 is a universal cable 4 fro connecting the endoscope 1 disconnectibly to a control unit (not shown) which contains a light source and a video processor.

Figure 3:
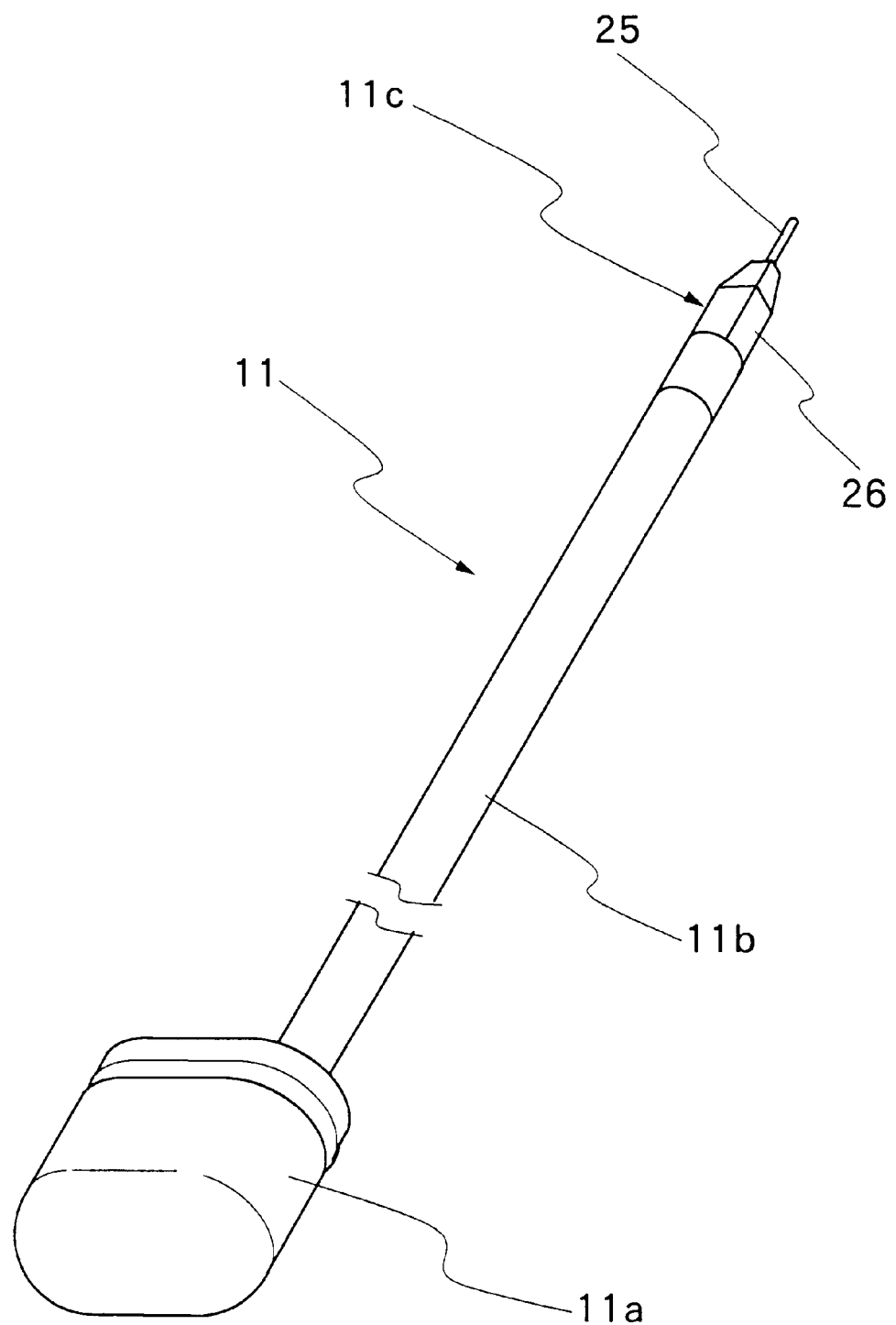
FIG. 3 is a schematic perspective view of the ultrasound probe as a whole.

The ultrasound examination system 10 includes an ultrasound probe 11, a probe controller 12 which is disconnectibly connected with the ultrasound probe 11, and an ultrasound image observation terminal 13 with a viewing or monitor screen 14. The ultrasound probe 11 to be introduced into a body cavity is provided with an ultrasound scanner head 11a at the distal end of a flexible cord 11b as shown in FIG. 3. At the opposite proximal end, the flexible cord 11b is terminated with a tail end connector 11c. This ultrasound probe 11 is introduced into a body cavity through a biopsy channel which is provided on the endoscope 1. In this instance, the endoscope 1 is provided with a couple of biopsy channels 5a and 5b which are provided coextensively within the endoscopic insertion instrument 3 as far as the distal end of the latter. The proximal ends of the respective biopsy channels 5a and 5b are connected to entrance passages 6a and 6b which are provided on the housing of the manipulating head grip 2. The other ends of the biopsy channels 5a and 5b are opened in the fore end face (or on a lateral side) of the endoscopic insertion instrument 3 in the vicinity of an endoscopic image pickup portion including an observation window and an illumination window. One of the two biopsy channels 5a and 5b, for example, the biopsy channel 5a is used for introducing the ultrasound probe 11 into a body cavity.

Figure 4:
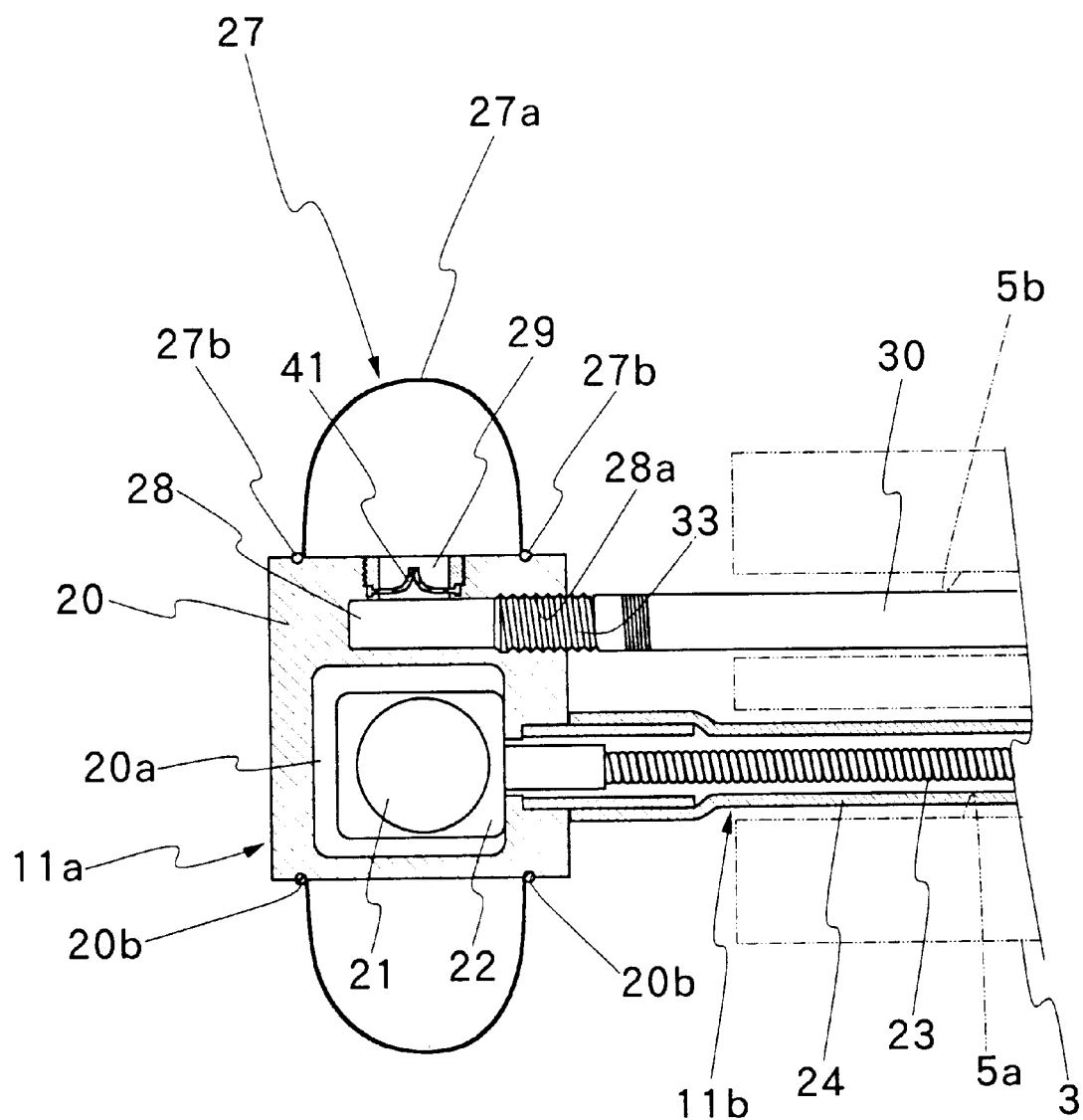
FIG. 4 is a schematic sectional view of a fore end portion of the ultrasound probe connected with the ultrasound transmission medium feed device.

As seen in FIG. 4, the ultrasound scanner head assembly 11a includes an end housing 20 which is formed of a synthetic resin material having favorable properties in ultrasound transmission in its entirety. Provided within the end housing 20 is a chamber 20a which accommodates a rotary base 22 for mounting an ultrasound transducer element 21. An ultrasound transmission medium such as liquid paraffin, for example, is filled in the internal space of the chamber 20a in a sealed state. The ultrasound transducer element 21 is rotationally driven by remote control for a scan in the rotational direction, that is to say, for a radial scan. For this purpose, the rotary base 22 which supports the ultrasound transducer element 21 is connected to a flexible transmission shaft 23 in the form of a tightly wound coil tube. On the other hand, the end housing 20 is connected to a flexible sheathing tube 24. Thus, the flexible cord 11b which is connected to the ultrasound scanner head 11a is constituted by the flexible sheathing tube 24 and the flexible transmission shaft 23 which is fitted in the sheathing tube 24 for rotation about the longitudinal axis thereof. In order to transmit rotation accurately and efficiently, the flexible transmission shaft 23 is preferably of double coil type consisting of two coils which are tightly wound in opposite directions from each other. A signal cable is passed axially through the internal space of the flexible transmission shaft 23.

Although not shown in the drawings, at least a rotational drive means for the ultrasound transducer element 21 and a rotational angle detection means are built into the probe controller 12, which is rotationally and electrically coupled with the ultrasound probe 11 through the tail end connector 11c which is provided at the proximal end of the flexible cord 11b of the probe 11. In addition to the function of rotationally driving the flexible transmission shaft 23 which is connected to the ultrasound transducer element 21, the probe controller 12 serves as a relay means for passing on ultrasound signals to and from the ultrasound image observation terminal 13 and the signal cable which is connected to the ultrasound transducer element 21 through the flexible transmission shaft 23. Accordingly, the tail end connector 11c of the ultrasound probe 11 includes a stationary part which is connected to the flexible sheathing tube 24 for retaining same fixedly relative to the probe controller 12, and a rotating part which is connected to the flexible transmission shaft 23 for coupling same with a rotational shaft provided on the probe controller 12. The rotating part of the tail end connector 11c is provided with an electrode pin 25 and an electrode ring 26.

The ultrasound transducer element 21 is of a large size which can transmit ultrasound signals into deep internal regions at the time of an ultrasound examination, and therefore the scanner head 11a accommodates the ultrasound transducer element 21 in the end housing 11a which is much larger than the inside diameter of the endoscopic biopsy channel 5a in which the ultrasound probe 11 is to be placed. Namely, the ultrasound scanner head 11a is too large in outside diameter for passage through the endoscopic biopsy channel 5a. Instead, the flexible cord 11b and tail end connector 11c are formed in a smaller diameter than the endoscopic biopsy channel, so that the ultrasound probe 11 can be inserted into the endoscopic biopsy channel 5a inversely from its proximal end with the tail end connector 11c, through an exit opening of the biopsy channel 5a opened at the distal end of the endoscopic insertion instrument 3. Then, the tail end connector 11c, which is at the leading end of the ultrasound probe 11 being inserted into the endoscopic biopsy channel 5a, is firstly led out of the biopsy channel 5a through the entrance passage 6a on the manipulating grip 3a of the endoscope 3 and coupled with the probe controller 12. Although not shown in the drawings, the probe controller 12 can be fixed on a housing of the entrance passage 6a or on the ultrasound image observation terminal 13 with or without the use of a support or mount member. In this case, in order to permit easy fixation of the probe controller 12 on the entrance way 6a of the biopsy channel 5a, it is desirable to provide a loosely looped extra portion in a proximal end portion of the flexible cord 11b.

While ultrasound pulses are transmitted from the ultrasound transducer element 21 of the scanner head 11a at predetermined angular intervals, it is necessary to stop an air gap which may intervene between the scanner head 11a and an intracavitary wall by inflating the balloon 27 which is fitted on the end housing 20 of the scanner head 11a. In the particular embodiment shown, the balloon 27 is constituted by a tubular membrane 27a of elastic material such as latex or the like, which has its opposite end portions hermetically stopped on the end housing 20 by stopper rings 27a and 27b. The stopper rings 27a and 27b are engaged with annular grooves 20b which are provided on and around the circumference of the end housing 20.

At the time of an ultrasound examination, an ultrasound transmission medium like deaerated water, for example, is introduced into the membrane 27a thereby inflating the balloon 27 until it comes into intimate contact with an intracavitary wall portion to which ultrasound signals are to be transmitted. As a result, the ultrasound transducer element 21 is allowed to take a suitable stand-off position relative to an intracavitary wall portion under examination without opening an air gap in the path of ultrasound signal transmission. In this case, however, the balloon 27 is inflated with the ultrasound transmission medium only at the time of an ultrasound examination, that is to say, it is necessary to hold the balloon in a contracted or deflated state unless the ultrasound probe is in use. Accordingly, it is after the ultrasound scanner head 11a has been located in an examination site within a body cavity that the ultrasound transmission medium is supplied to and from the balloon 27 through medium supply passages which will be described hereinlater.

Figure 5:
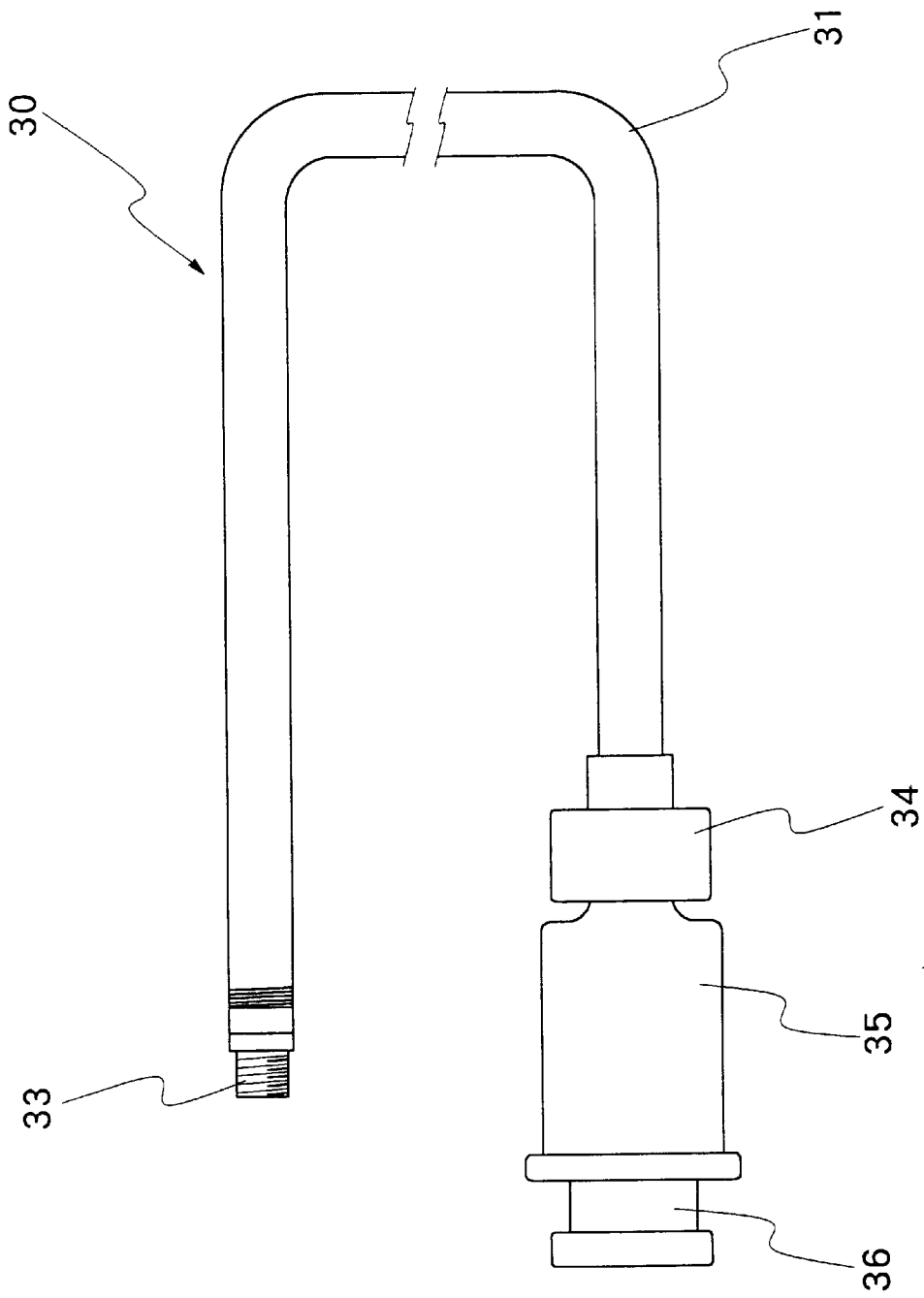
FIG. 5 is a schematic view of the ultrasound transmission medium feed device as a whole.
Figure 6:
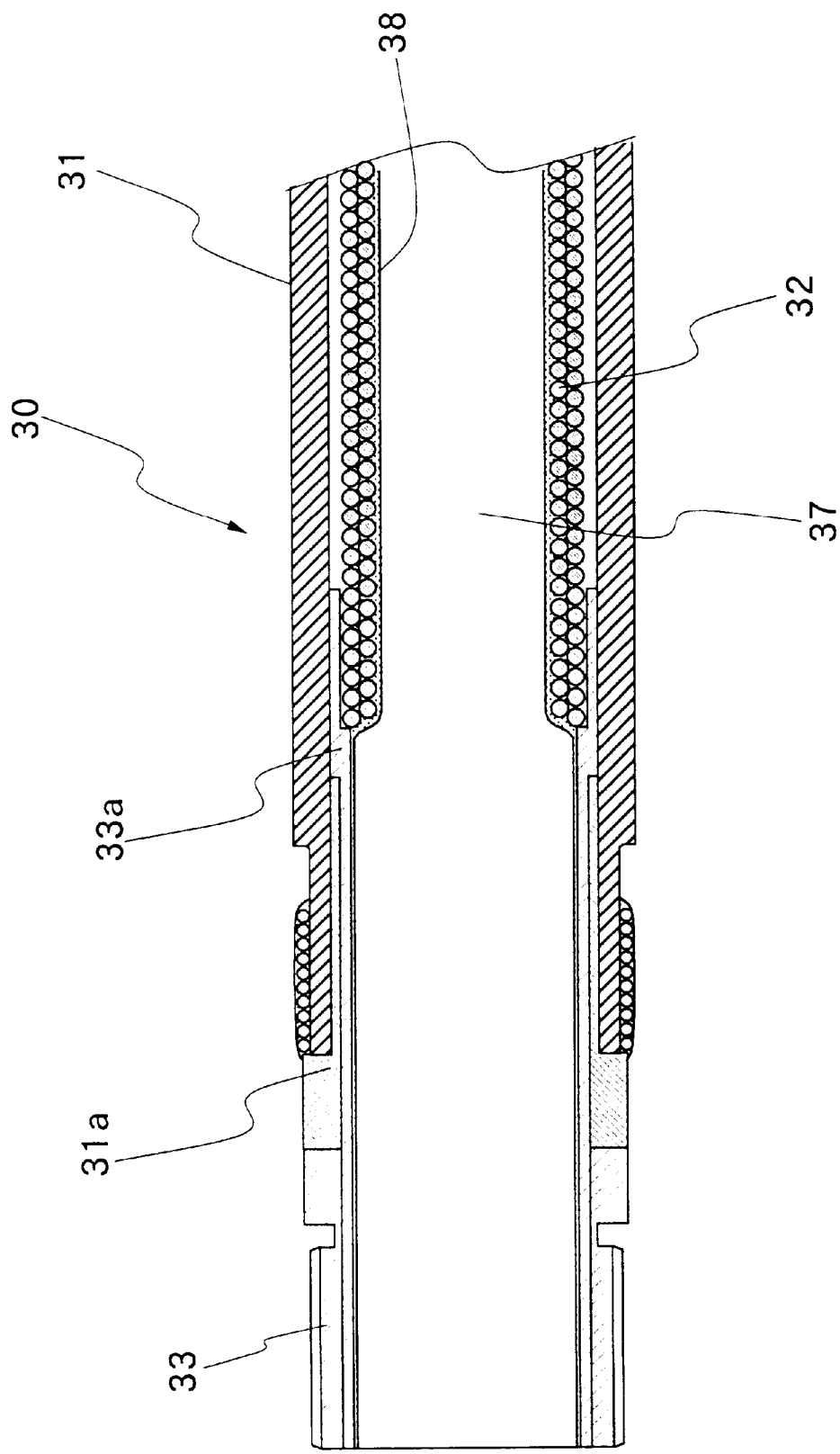
FIG. 6 is a schematic view on an enlarged scale of a fore end portion of the ultrasound transmission medium feed device shown in FIG. 5.
Figure 7:
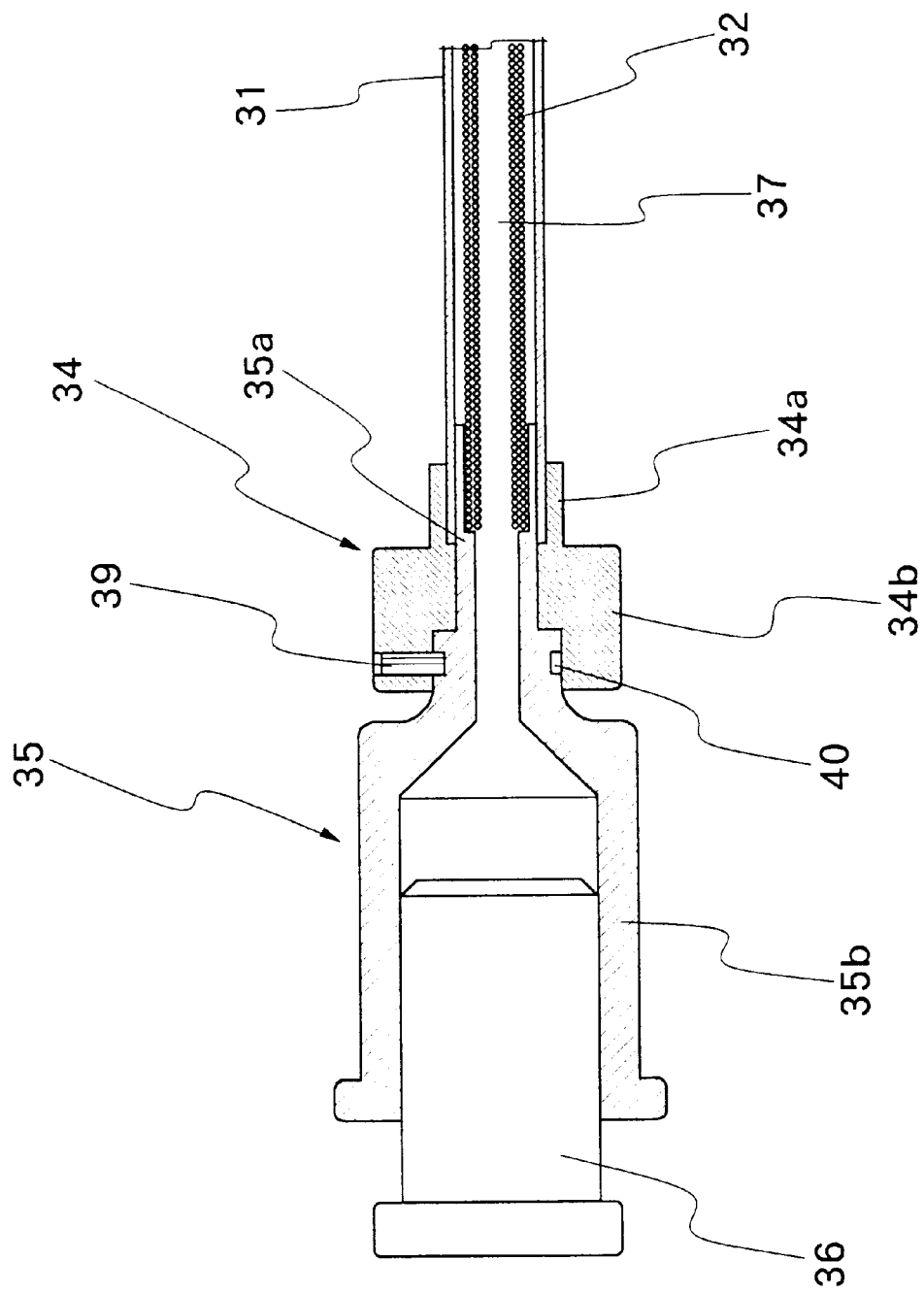
FIG. 7 is a schematic view on an enlarged scale of a proximal end portion of the ultrasound transmission medium feed device shown in FIG. 5.

A passage for the supply of the ultrasound transmission medium is secured by utilizing other one of the two endoscopic biopsy channels 5a and 5b which are provided on the endoscope 1, that is to say, through the other biopsy channel 5b which is not used as a guide passage for the ultrasound probe 11 itself at the time of introduction into a body cavity. The other biopsy channel 5b is normally used either for sending a wash liquid into a body cavity or for insertion of other instruments, for example, an instrument for sucking out body fluids, so that its use as a medium supply passage should not impair these originally intended functions of the biopsy channels. Therefore, an ultrasound transmission medium feed device is removably fitted in the second endoscopic biopsy channel 5b. Shown in FIGS. 5 to 7 is an example of such an ultrasound transmission medium feed device.

More specifically, shown in these figures is an ultrasound transmission medium feed device 30 in the form of a pressurizing feed tube including a flexible feed sleeve 31 which has a rigid pipe 31a connected to its distal end. As shown particularly in FIG. 6, a coil tube, with double-layer tightly wound coils 32, is fitted in the feed tube 31. Fore ends of the tightly wound coils 32 are securely or integrally fixed to a connecting ring portion 33a of an annular ring-like male screw member 33. As the male screw member 33 is rotationally driven by the tightly wound coils 32, the connecting ring portion 33a of the screw member 33 is turned in sliding contact with inner periphery of a rigid pipe member 31a which is connected to the fore end of the sleeve 31.

The pressurizing feed tube 30 is provided with an operating portion at its proximal end for rotating the screw member 33 by remote control, along with a medium feed portion for sending forward an ultrasound transmission medium like deaerated water under pressure. The operating portion of the pressurizing feed device is largely constituted by a stationary member and a rotating member. Indicated at 34a in FIG. 7 is a stationary member, including a connecting portion 34a, which is securely fixed to the sleeve 31, and a retainer portion 34b which is larger in diameter than the connecting portion 34a. On the other hand, the rotating part which is indicated at 35 is constituted by a connecting portion 35a, which is fitted in the stationary part 34 and connected at its fore end to the proximal end of the tightly wound coils 32, and a cylinder portion 35b of a larger diameter which is provided contiguously at the proximal end of the connecting portion 35a. A pressurizing member, which is a piston 36 in the particular embodiment shown, is axially slidably fitted in the cylinder portion 35. Accordingly, the cylinder portion 35 internally defines a deaerated water reservoir of a variable volume in cooperation with the pressurizing member 36.

Each one of the screw member 33, the rotational operating member 34 and the tightly wound coils 32, which is connected axially between the screw member 33 and the operating member 34, is in a hollow cylindrical or tubular shape, so that a fluid supply passage 37 can be provided axially and internally through these component parts. More specifically, a fluid supply passage 37 is provided within an inner coat layer 38 of a flexible thin film which is coated on the inner periphery of the feed tube 30 from the screw member 33 to the rotating member 33 through the coil tube 32 thereby to prevent leaks of fluid medium to the outer peripheral side of the coil tube 32.

On the part of the ultrasound probe 11, a fluid passage or an inlet-outlet passage 28 for the ultrasound transmission medium is bored into the end housing 20 of the ultrasound scanner head assembly 11a in its base end portion which is connected to the flexible cord 11b. The fluid inlet-outlet passage 28 is provided with an internal screw portion 28a at its outer end for threaded engagement with the male screw member 28 of the feed tube 30. The fluid passage 28 is communicated at its inner end with a communication port 29 which is opened on a lateral side of the end housing 20 on the side away from the chamber 20a. Upon supplying an ultrasound transmission medium to the fluid passage 28, it is introduced into the space between the end housing 20 and the elastic membrane 27a of the balloon 27 through the communication port 29 to expand the balloon 27 into an inflated state. Thus, the fluid passage 28 and the communication port 29 constitute an inlet-outlet port for the ultrasound transmission medium to be charged or discharged into or out of the balloon 27.

The pressurizing feed tube 30 is placed in the endoscopic biopsy channel 5b and detachably connected to the fluid passage 28 of the end housing 20. The pressurizing feed tube 30 has a length which is greater than the overall length of the endoscopic biopsy channel 5b, and placed in the latter through an entrance passage 6b on the housing of the manipulating grip of the endoscope 1. In use, after fixing the retainer portion 34b of the stationary part 34 on the entrance passage 6b, the rotary part 35 is turned with fingers, whereupon the rotation of the rotary part 35 is transmitted to the screw member 33 through the tightly would coil tube 32. Accordingly, by rotation of the rotary part 35 of the feed tube 30, the screw member 33 is urged into threaded engagement with the internal screw portion 28a of the fluid passage 28 and securely connected with the latter. For this purpose, the rotary part 35 should be rotatable relative to the stationary part 34 but should be blocked against movements in the axial direction. To this end, a pin 39 which is provided on the stationary part 34 is 11 engaged with an annular groove 40 which is formed on the circumferential surface of the connecting portion 35a of the rotary part 35.

By the use of the pressurizing feed tube 30, which is arranged as described above, an ultrasound transmission medium such as deaerated water, for example, is charged into or discharged from the balloon 27 which is fitted on the ultrasound scanner head 11a at the distal end of the probe 11, thereby to inflate the balloon 27 with the ultrasound transmission medium or to deflate the balloon 27 into a contracted state. The deaerated water inlet-outlet passage which is formed in the end housing 20 of the ultrasound scanner head 11a by way of the above-described passage 28 and communication port 29 is preferred to contain a check valve 41 in a suitable position, for example, at a position between the passage 28 and the communication port 29 as shown particularly in FIGS. 8 and 9.

Figure 8:
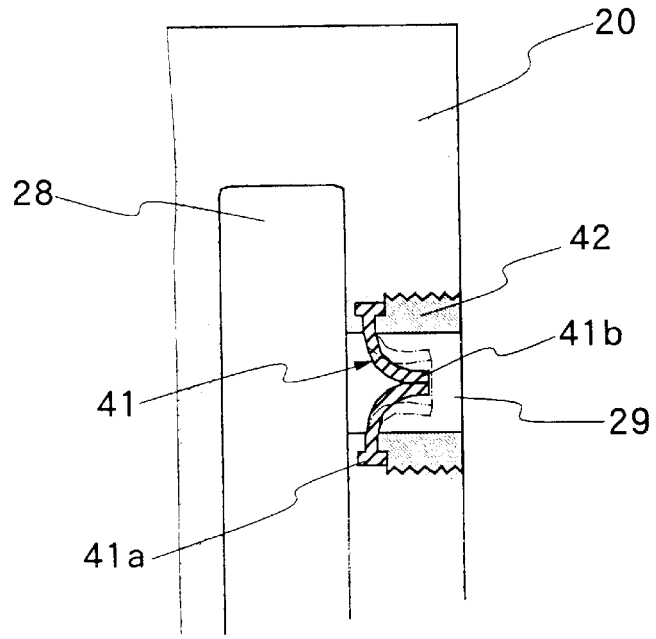
FIG. 8 is a schematic sectional view of a check valve.

The check valve 41 is formed of a resilient material like rubber, generally in a hollow truncated cone shape, and provided with an annular anchor portion 41a at its base end. The truncated end of the check valve 41, at the end away from the annular anchor portion 41a, is folded into a flat form, so that a valve portion 41b is formed by opposing wall portions which are folded into intimate contact with each other in the fashion of lips. The flatly folded wall portions which form the valve portion 41b are thinned down in thickness and provided with slits. The check valve 41 is fixed in position between the fluid passage 28 and the communicating port 29 by means of a stopper ring 42 which is threaded into the communicating port 29. When lips of the valve portion 41b 11 are projected outward or toward the communicating port 29 as shown in FIG. 8, the check valve functions to restrict a flow of fluid into the passage 28 from the side of the communication port 29. On the contrary, when lips of the valve portion 41b are projected inward or into the passage 28, the valve functions to restrict a flow of fluid into the communicating port 29 from the side of the passage 28.

Thus, when no pressure differential exists across the valve portion 41b, it remains closed. When in the position shown in FIG. 8, if the pressure on the side of the passage 28 becomes higher than the pressure on the side of the communicating port 29, the prevailing pressure acts on the inner surfaces of the valve portion 41b to spread apart the valve lips as indicated by imaginary line, permitting a fluid to flow toward the communicating port 29 from the side of the passage 28. On the other hand, even when a higher pressure is built up on the side of the communicating port 29, there will occur no fluid flow into the passage 28 from the side of the communicating port 29. However, this is true as long as the pressure differential is smaller than a predetermined value which is determined by the stiffness of the valve portion 41b. When a vacuum s pressure occurs on the side of the passage 28 to widen the pressure differential, the valve portion 41b is reversed to the position shown in FIG. 9. By the reversal of the valve portion 41b, the flow direction of fluid is also reversed. Namely, when the pressure differential across the valve portion 41b becomes larger than a predetermined value, the valve allows a fluid to flow into the passage 28 from the side of the communication port 29, prohibiting the fluid to flow in the reverse direction. It follows that the balloon 27 can be retained in an inflated state with a suitable amount of deaerated water by setting the reversing point of the check valve 41 at a pressure higher than the internal pressure of the balloon which has been inflated to a predetermined degree, for example, by introduction of a certain amount of deaerated water.

After placing the ultrasound probe 11 in a biopsy channel of the endoscope 1 in the manner as described above, the endoscopic insertion instrument 3 is introduced into a body cavity. At this time, although the ultrasound scanner head 11a is projected forward from the distal end of the endoscopic insertion instrument 3, the path of insertion can be easily confirmed by way of the endoscopic observation system because the dimension of the ultrasound scanner head 11a is limited to a size which would not block the view field of the endoscopic observation. Further, the ultrasound scanner head 11a which is connected at the distal end of the flexible cord 11b can be retained in a stabilized state by pulling the flexible cord 11b into the endoscopic biopsy channel 5a. Therefore, when assembled into the endoscope 1, there is no possibility of the ultrasound probe 11 blocking movements of the endoscopic insertion instrument 3 as the latter is inserted into a body cavity.

After inserting the endoscope 1 into an aimed site of examination within a body cavity, an intracavitary region of particular interest is examined firstly by the endoscopic observation system, and, if a diseased portion is spotted by the endoscopic observation system, it is further examined by an ultrasound scan. For an ultrasound examination, firstly a predetermined amount of deaerated water or other ultrasound transmission medium is supplied to the balloon 27 which is fitted on the ultrasound scanner head 11a. For this purpose, the ultrasound transmission medium feeder device 30 is placed in the other biopsy channel 5b of the endoscope 1. The medium feeder device 30 is internally provided with a medium supply passage 37 coextensively along its entire length, and the proximal end of the medium supply passage 37 is terminated with the rotary part 35 of an increased diameter including the cylinder portion 35b and the pressurizing means 36. Accordingly, upon pulling the pressurizing means 36 out of the cylinder portion 35 to a certain extent, deaerated water is filled in the cylinder portion 35b and in the entire spaces of the medium supply passage 37.

Figure 9:
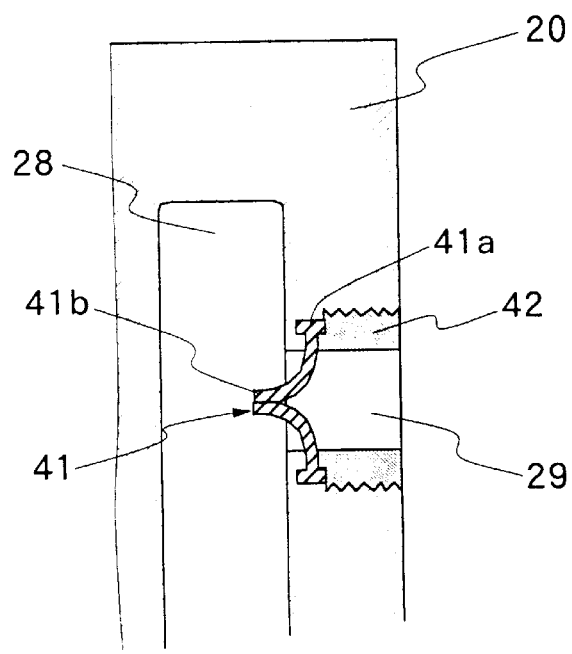
FIG. 9 is a view similar to FIG. 8 but showing the check valve in a different phase of operation.

Then, the fore end of the pressurizing feed tube 30 is projected from the fore end of the endoscopic biopsy channel 5b, urging the screw member 33 into engagement with the passage 28 of the end housing 30. In this regard, the fore end portion of the medium feed tube 30 can be easily directed toward the passage 28 on the end housing 30 by arranging the ultrasound probe 11 such that the passage 28 is brought into axial alignment with the endoscopic biopsy channel 5b when the ultrasound probe 11 is placed into the endoscopic biopsy channel 5a fully until the ultrasound scanner head 11a comes to the proximity of the fore end face of the endoscopic insertion instrument 3. With the screw member 33 in engagement with the passage 28, rotation is transmitted to the screw member 33 through the double coil tube 32 upon turning the rotary member 35 while holding the retainer portion 34b of the stationary member 34 in a fixed state. Whereupon, by rotation, the screw member 33 is threaded into the internal screw 28a formed on the inner periphery of the passage 28. As a result, the ultrasound transmission medium feed tube 30 is connected with the ultrasound scanner head 11a of the probe 11. 15 Then, the pressurizing member 36 is pushed inward of the cylinder 36, whereupon deaerated water in the cylinder 36 is sent forward to the fluid feed passage 37 under pressure and then to the passage 28. At this time, the check valve 41, which is provided between the passage 29 and the communication port 29, is set in the position shown in FIG. 8 to let the pressure prevailing on the side of the passage 28 flow into the communicating port 29. As a result, the pressurized medium is introduced into the balloon 27 to inflate same to a predetermined degree. It is probable that air is allowed to enter the balloon 27 at the time of connecting the feed tube 30, but such air should be expelled out of the balloon 27 if any. For this purpose, once the balloon 27 is inflated, the ultrasound scanner head 11a of the probe 11 is turned downward to let air climb upward within the balloon 27, and the pressurizing member 36 is pulled out of the cylinder 35b until the check valve 41 is reversed as shown in FIG. 9 to discharge air from the balloon 27. If the check valve 41 is left in this reversed position, it can be opened by the action of the pressure accumulated in the balloon 27 unless a counter pressure is applied on the side of the passage 28. In order to avoid this problem, it is desirable to apply a pressure on the pressurizing member 36, thereby reversing the check valve 41 again to the position of FIG. 8 to prevent inverse flow of deaerated water out of the balloon 27. In case a high pressure is constantly maintained on the side of the passage 28, the reversal of the check valve 41 is not necessarily required in preventing such an inverse flow of deaerated water from the balloon 27.

When inflated, the balloon 27 is brought into abutting contact with an intracavitary wall in the site of an ultrasound examination. In this state, the ultrasound transducer element 21 is rotationally driven for a radial scan to produce an ultrasound image which gives information on body tissues in the scanned regions. The ultrasound scanner head 11a of the probe 11 can employ an ultrasound transducer element with a large active surface area because it is free from the restrictions as normally imposed by the inside diameter of the endoscopic biopsy channel 5a. Accordingly, this type of ultrasound scanner head can obtain tomographic information in deeper positions within the patient's body. Further, especially in the case of an ultrasound scan at a position immediately beneath the mucous, it is possible to maintain the ultrasound transducer element in a suitable stand-off position relative to an intracavitary wall under observation by varying the degree of inflation of the balloon 27 which is abutted against the intracavitary wall. Furthermore, attenuations of return echo signals can be suppressed to a minimum by the exclusion of air from the path of ultrasound signals.

Thus, the ultrasound probe 11 can make ultrasound scans in an extremely accurate manner. Upon finishing an ultrasound examination, the balloon 27 needs to be contracted into the original deflated state. To this end, the pressurizing member 36 is pulled out of the cylinder 35a to a certain degree, whereupon vacuum pressure is developed in the cylinder 35a by expansion of its volume, causing the check valve 41 to reverse its lips to the position of FIG. 9 if they were in the position shown in FIG. 8, permitting to collect deaerated water from the balloon 27. As soon as deaerated water is completely collected from the balloon 27, the rotary member 35 is turned within the stationary member 34 to disengage the screw member 33 of the feed tube 30 from the internal screw portion 28a of the passage 28. Accordingly, the feed tube 30 can now be extracted from the endoscopic biopsy channel 5a. Upon extraction of the feed tube 30, the endoscopic biopsy channel 5a is left in a free state and can be used for its originally intended functions, for example, as a channel for sending a liquid into the body cavity or for sucking body fluids out of the body cavity or as a channel for inserting a bioptic or surgical instrument.

Figure 10:
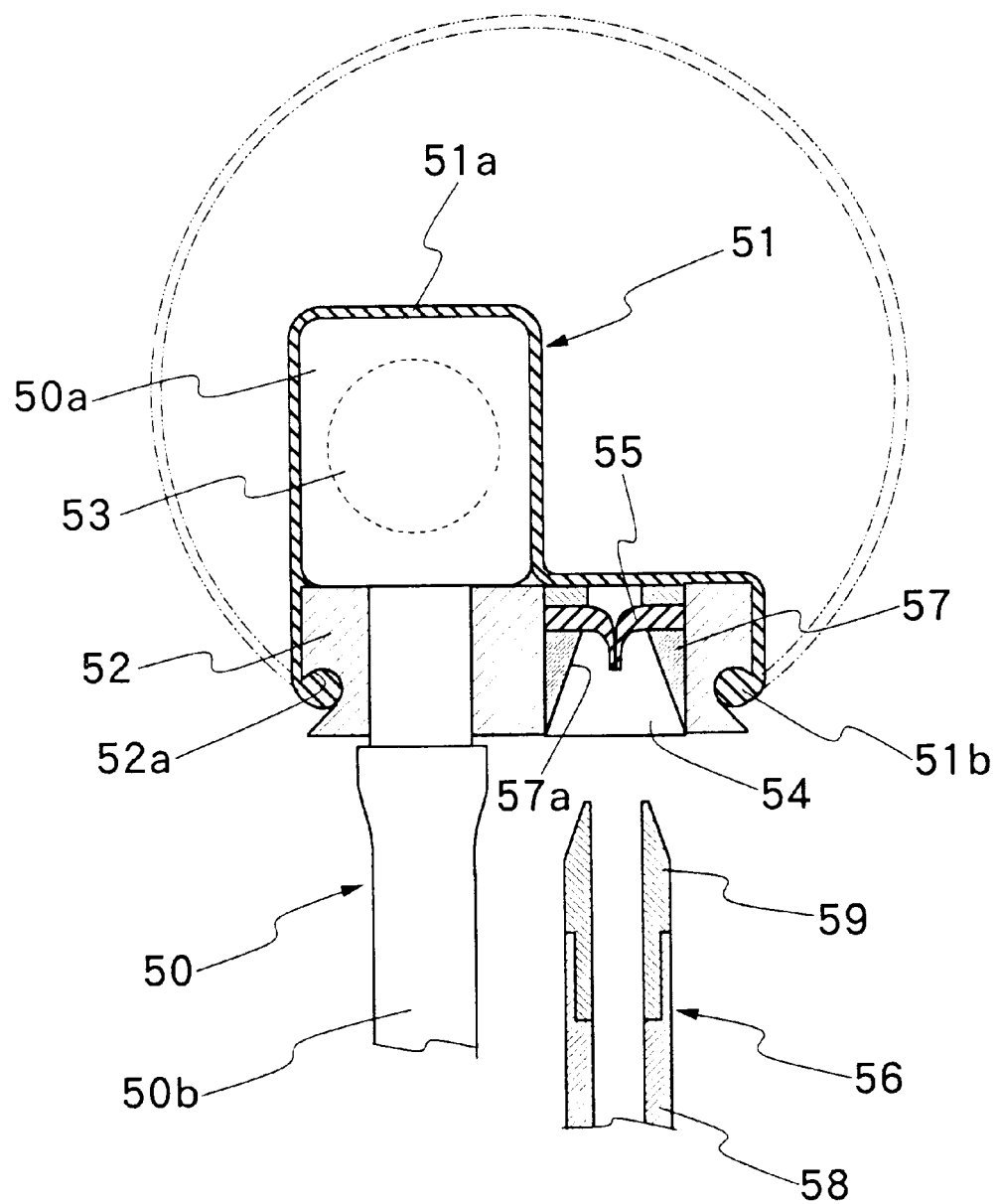
FIG. 10 is a schematic sectional view showing a fore end portion of an ultrasound probe along with an ultrasound transmission medium feed device with a modified tip end.

Turning now to FIG. 10, there is shown another embodiment of the present invention. In this figure, indicated at 50 is an ultrasound probe which is placed in one of biopsy channels of an endoscope beforehand, and at 51 is a balloon which is attached not directly to an end housing of an ultrasound scanner head 50a of the ultrasound probe 50 but indirectly through a mount plate 52 which is fixed to the base end of the scanner head 50a. Connected to the base end of the scanner head 50a through the mount plate 52 is an elongated flexible cord 50b which is provided with a tail end connector at its proximal end, similarly to the tail end connector 11c of the foregoing first embodiment, for coupling the ultrasound probe 50 disconnectibly with a probe controller although not shown in the drawing. Provided internally of the ultrasound scanner head assembly 50a is an ultrasound transducer element of a large size, which can be scanned in the radial direction by remote control and through a flexible transmission shaft fitted in the flexible cord 50b.

The balloon 51 consists of an elastic membrane 51a with an annular stopper ring 51b, which engages in an annular groove 52a provided on the part of the mount plate 52. In this instance, the mount plate 52 itself may be of a circular shape but it is preferred to be a plate of an elliptic shape and have a sufficient thickness for stably holding the stopper ring 51a of the balloon 51. The mount plate 52 is provided with a through hole 54 across its thickness as a passage for deaerated water to be supplied into the balloon 51. Further, preferably, a check valve 55 is fitted in the passage 54. A pressurizing feed tube 56, which inflates the membrane 51a of the balloon 51 with the ultrasound transmission medium as indicated by imaginary line in FIG. 10, is provided with an ultrasound transmission medium feed portion at its proximal end, including a cylinder portion and a pressurizing member similar to the ones shown in the foregoing embodiment. In this case, in order to guide a fore end portion of the pressurizing feed tube 56 smoothly toward the passage 54 and connect same fixedly it to the latter easily without necessitating a rotating operation, a magnet 57 with an outwardly diverging tapered hole 57 is fixedly fitted in the passage 54 on the part of the scanner head 51 thereby while a correspondingly tapered tip member of magnetic material is attached to the distal end of a flexible tube member 58 of the pressurizing feed tube 56.

With the arrangements just described, thanks to the guiding actions of the magnet 59 in the mount plate 52 and the tapered hole in the magnet 59, the tipped end 59 of the pressurizing feed tube 56 is automatically urged into a coaxially centered position within the passage 54 and connected with the latter as soon as it is brought to the proximity of the magnet 57. Accordingly, in this case, there is no necessity for providing a remote-control rotational drive mechanism as in the above-described first embodiment. Besides, at the time of sending forward deaerated water under pressure from the pressurizing feeder tube, the reaction forces which tend to move the mount plate 52 away from the pressurizing feed tube 56 can be effectively born by the magnetic attracting force between the magnet 57 and the tip 59. When recovering deaerated water from the balloon 51 at the end of an ultrasound examination, there is no possibility of the mount plate 52 being separated from the pressurizing feeder tube 56 because it is constantly pressed against the latter.

What is claimed is:

1. In an ultrasound examination system having an endoscopically inserting ultrasound probe adapted to be introduced into a body cavity through and under guidance of one of biopsy channels provided on an endoscope, said ultrasound probe having an ultrasound scanner head at the distal end of an elongated flexible cord, said ultrasound scanner head accommodating an ultrasound transducer element rotatably within an end housing of such a large size as to necessitate to place said ultrasound probe in said one biopsy channel from the opposite proximal end of said flexible cord terminated with a thin and narrow tail end connector:

an ultrasound transmission medium feed device, comprising:

a balloon fitted on a base end portion of said ultrasound scanner head fixedly in a hermetically sealed state in such a way as to wrap in said end housing of said scanner head;

an inlet-outlet passage provided on said base end portion of said ultrasound scanner head for charging and discharging an ultrasound transmission medium into and out of said balloon through a communicating port; and a pressurizing feed tube adapted to be placed in another biopsy channel of said endoscope and disconnectibly connectible at a fore distal end portion thereof with said inlet-outlet passage on said ultrasound scanner head, said feed tube having a pressurizing member in a proximal end portion thereof for pressurizing or depressurizing the ultrasound transmission medium to be supplied to said inlet-outlet passage on said ultrasound scanner head.

2. An ultrasound transmission medium feed device as defined in claim 1, wherein said pressurizing feed tube is provided with an external screw member on a distal end portion for threaded engagement with an internal screw provided in said inlet-outlet passage on said ultrasound scanner head.

3. An ultrasound transmission medium feed device as defined in claim 2, wherein said pressurizing feed tube has an external screw member connected to a distal end portion of a flexible coil shaft fitted in said flexible tube, said screw member being rotatable from a remote rotating means connected to a proximal end portion of said flexible coil shaft.

4. An ultrasound transmission medium feed device as defined in claim 1, wherein said pressurizing feed tube is adapted to be fixedly connected to said inlet-outlet passage on said ultrasound scanner head by means of a magnet.

5. An ultrasound transmission medium feed device as defined in claim 1, wherein said inlet-outlet passage is provided with an inwardly converging tapered wall for automatically guiding said pressurizing feed tube into a coaxially aligned position.

6. An ultrasound transmission medium feed device as defined in claim 1, further comprising a check valve interposed between said inlet-outlet passage and said communicating port.

7. An ultrasound transmission medium feed device as defined in claim 6, wherein said check valve is adapted to reverse flow direction of said ultrasound transmission medium as soon as a pressure differential thereacross exceeds a preset value.

* * * * *